United States Patent [19]

Hunt et al.

[11] Patent Number: 5,003,184

[45] Date of Patent: Mar. 26, 1991

[54] LOW TEMPERATURE INFRARED SOURCE

[75] Inventors: Robert N. Hunt, Wheeling; Robert L. Sandridge, Proctor, both of W. Va.

[73] Assignee: Mobay Corporation, Pittsburgh, Pa.

[21] Appl. No.: 398,692

[22] Filed: Aug. 25, 1989

[51] Int. Cl.$^5$ .................................................. G01J 1/00
[52] U.S. Cl. ................................ 250/504 R; 250/453.1
[58] Field of Search ........................ 250/493.1, 504 R

[56] References Cited

U.S. PATENT DOCUMENTS

| | | | |
|---|---|---|---|
| 3,784,836 | 1/1974 | Tolliver | 250/504 R |
| 4,337,396 | 6/1982 | Lauer | 250/340 |
| 4,499,382 | 2/1985 | Vincent | 250/504 R |
| 4,618,771 | 10/1986 | Farren | 250/343 |
| 4,639,603 | 1/1987 | Pistor | 250/493.1 |
| 4,681,445 | 7/1987 | Perkins | 356/346 |
| 4,724,329 | 2/1988 | Doyle et al. | 250/504 R |
| 4,740,082 | 4/1988 | Young | 356/346 |
| 4,795,253 | 1/1989 | Sandridge et al. | 356/51 |
| 4,859,858 | 8/1989 | Knodle | 250/504 R |

Primary Examiner—Bruce C. Anderson
Attorney, Agent, or Firm—Joseph C. Gil; Lyndanne M. Whalen

[57] ABSTRACT

An infrared source suitable for use as a remote source for infrared interferometer spectrometers. This device is composed of a heat source, a black body radiating element and a concave reflector. A support to maintain the heat source and black body radiating elements in proper position is also preferably included. The device of the present invention enhances the accuracy and sensitivity of gas sensing devices based upon measurement of background infrared radiation, and allows the remote infrared source to be used in locations in which ignitable materials may be present.

6 Claims, 1 Drawing Sheet

LOW TEMPERATURE INFRARED SOURCE

BACKGROUND OF THE INVENTION

The present invention relates to a low temperature infrared radiation source.

Use of an infrared source to provide a radiation source which essentially matched the radiation of the source to the throughput radiation of an interferometer spectrometer is known. For example, U.S. Pat. No. 4,724,329 discloses an infrared source which is composed of a radiating element positioned at the center of a hollow, inwardly reflecting sphere having a single aperture positioned to fill the entrance field of view of a spectrometer with infrared radiation. This infrared source is, however, contained in the disclosed interferometer and does not function as a remote source. Further, the temperatures present in this source are undesirably high, particularly if the device is to be located in an area in which significant amounts of volatile, ignitable materials are present.

U.S. Pat. No. 4,681,445 also discloses an interferometer in which a radiation source is incorporated. The details of this radiation source are not given but it is clear from the disclosure that use of the radiation source external to the interferometer was not contemplated.

U.S. Pat. No. 4,740,082 also discloses a spectrophotometer in which an infrared radiation source beam is employed. In this disclosure, it is taught that the source beam may be positioned within the enclosure of a spectrophotometry instrument or external to the instrument. This disclosure does not, however, teach a specific instrument which employs an infrared source external to the device. The radiation source employed is a heated wire which provides radiation between the wavelengths of 5000 and 50 wavenumbers in the infrared spectrum. Such heated wire could not, however, be used as an external remote infrared source in an area where volatile materials might be present in significant quantities without substantial risk of fire or explosion.

In view of the greater flexibility of a remote source spectrophotometer, it would be advantageous to have an infrared radiation source which is external to the spectrophotometer that did not generate temperatures which would preclude its use in areas where volatile chemicals might be present in significant quantities.

SUMMARY OF THE INVENTION

It is an object of the present invention to provide a remote source of infrared radiation which may be used in any area to be monitored, even an area in which significant amounts of volatile, flammable materials may be present.

This and other objects which will be readily apparent to those skilled in the art are accomplished by a device composed of a heat source, a black body radiator which surrounds the heat source, a concave reflector and if necessary, a support to maintain the heat source in its proper position within the concave reflector.

DETAILED DESCRIPTION OF THE PRESENT INVENTION

The present invention relates to a low temperature remote source of infrared radiation useful in connection with infrared spectrophotometers, particularly gas sensing devices such as those described in U.S. Pat. No. 4,795,253. The device of the present invention is composed of a heat source, a black body radiating element, a concave reflector and if necessary, a support to hold the heat source in its proper position within the reflector.

Figure 1:
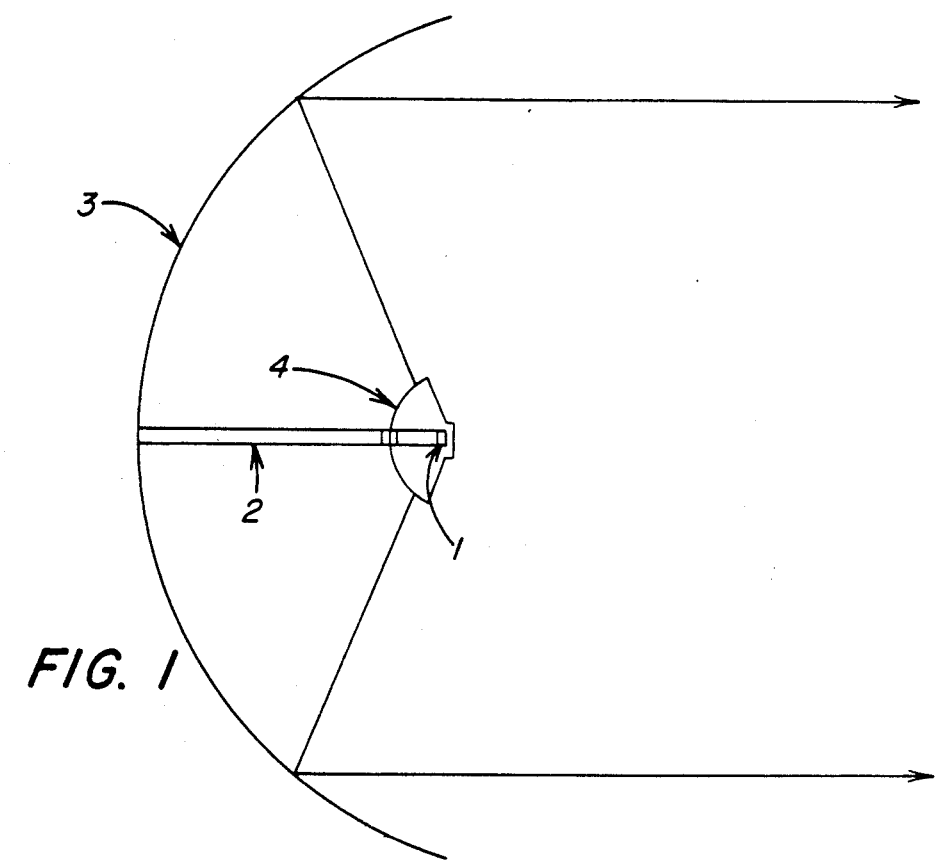
FIG. 1 illustrates one embodiment of the remote source of the present invention.

One embodiment of such a device is shown in FIG. 1 in which heat source 1 is mounted on support 2 which is mounted on concave reflector 3. Heat source 1 is completely surrounded or encased by black body radiating element 4.

Heat source 1 may be any device capable of raising the surface temperature of radiating element 4 to required levels. Specific examples of such devices include heating cartridges, wire heating elements, ceramic heating elements, quartz encased wire heaters and the like. The size of an appropriate heat generating device will of course depend upon the size of the black body radiating element 4 and the required power output of the source. The size of heat source 1 will also determine whether or not support 2 is needed. If support 2 is necessary, it is generally made of a durable material capable of withstanding the heat generated by heat source 1 without deterioration. Specific examples of suitable materials include stainless steel, ceramic, and chrome alloys. Where a support is employed, that support is generally long enough to maintain heat source 1 in the center of black body radiating element 4 and at the approximate focal point of concave reflector 3.

Reflector 3 may be parabolic, spherical or an approximation of these shapes. Reflector 3 is generally made of a material capable of withstanding a harsh environment such as rhodium plated electroformed nickel. The size of reflector 3 is dependent upon the area required for proper operation of the particular remote spectrometer employed, and will generally range from 3" to 36" in diameter. Heat source 1 and the surrounding radiating element 4 are generally positioned at the focal point of reflector 3, so as to collimate the outgoing infrared beam.

Figure 2A:
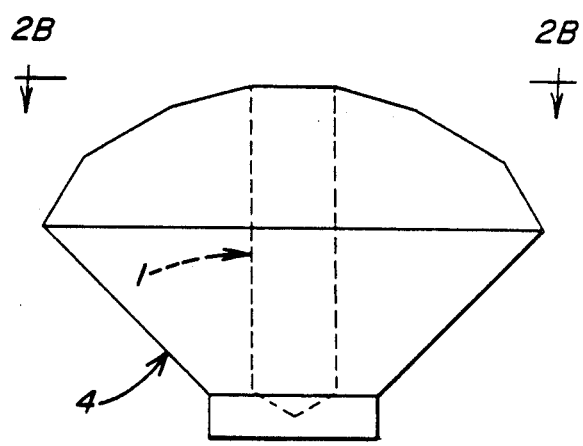
FIG. 2 illustrates a convex black body radiating element suitable for use in the remote source of the present invention.
Figure 2B:
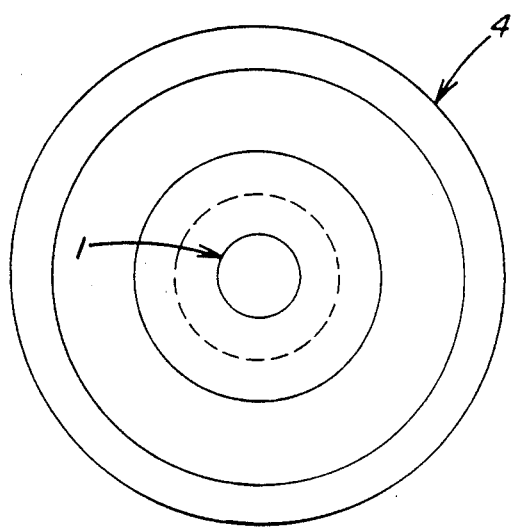

Black body radiating element 4 acts as a heat sink for the heat generated by heat source 1. Black body radiating element 4 reduces the radiating surface temperature generated by heat source 1 but maintains the thermal output of heat source 1. The black body element also shifts the spectral maximum from the visible and near infrared regions to longer infrared wavelengths. Black body radiating element 4 is generally made of a material capable of withstanding the temperatures generated by heat source 1 and the chemical environment of the area in which it is to be placed. Specific examples of suitable materials include brass, copper, stainless steel, and alloys having high thermal conductivity. The shape of black body radiating element 4 facing the reflector 3 is generally rounded or parabolic, preferably, with a diameter in the range of 0.5 to 0.028 of the diameter of reflector 3. A particularly advantageous shape is illustrated in FIG. 2. The inner surface of black body radiating element 4 is chemically blackened to improve emissivity. Techniques for blackening surfaces are known to those skilled in the art and any one of the known techniques may be employed. An example of such a technique is to treat the brass or copper with a solution containing 1 part copper carbonate, 2 parts aqueous ammonia, 5 parts water at 175° F. followed by dipping in a 2½% solution of caustic soda.

As has already been mentioned, the device of the present invention is advantageously used in combination with spectrophotometric devices such as the one disclosed in U.S. Pat. No. 4,795,253. More specifically, the device of the present invention may be positioned at a location between 15 and 500 meters from the gas sensing device. The radiation emitted by the device of the present invention is picked up by the gas sensing device and absorption bands due to gases in the beam path between the devices and are used to determine the presence and amounts of each gas.

Having thus described our invention, the following examples are given as being illustrative thereof. All parts and percentages given are parts by weight and percentages by weight, unless otherwise indicated.

EXAMPLES

EXAMPLE 1

A device corresponding to that illustrated in FIG. 1 was constructed from the following:

Heat source 1: a 250 Volt Amp ½ inch diameter Cromolox heater cartridge.

Support 2: a 14 inch length of ½ inch diameter stainless steel tube.

Concave reflector 3: a rhodium plated 24 inch parabolic reflector (available from Optical Radiation Corp.)

Black body radiating element 4: machined brass element which was chemically blackened.

This device was then positioned 60 meters from the gas sensing device described in Example 1 of U.S. Pat. No. 4,795,253 which is herein incorporated by reference. A 100 milligram sample of dichlorodifluoromethane was released into the atmosphere between the infrared source and the instrument. A spectrum of the halocarbon was obtained in approximately 3 seconds.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A low temperature infrared radiation source comprising
   (a) a heat source,
   (b) a black body radiating element which surrounds heat source (a) acting as a heat sink, and
   (c) a concave reflector positioned to reflect the radiant energy emitted by (b).

2. The device of claim 1 in which (d) a support element is employed to maintain the heat source (a) and radiating element (b) in proper position with respect to concave reflector (c).

3. The device of claim 1 in which heat source (a) is a heater cartridge.

4. The device of claim 1 in which radiating element (b) has a convex hemispheric or parabolic surface facing reflector (c).

5. The device of claim 1 in which reflector (c) is a parabolic mirror.

6. The device of claim 1 in which reflector (c) is a hemispherical mirror.

* * * * *